United States Patent [19]

Notoya et al.

[11] Patent Number: 5,244,577

[45] Date of Patent: Sep. 14, 1993

[54] PROCESS FOR PREPARING OSTEOGENESIS PROMOTING SUBSTANCE

[75] Inventors: Kohei Notoya, Settsu; Keiji Yoshida, Kawanishi; Iwao Yamazaki, Takarazuka, all of Japan

[73] Assignee: Takeda Chemical Industries, Ltd., Osaka, Japan

[21] Appl. No.: 7,801

[22] Filed: Jan. 22, 1993

Related U.S. Application Data

[63] Continuation of Ser. No. 755,007, Sep. 5, 1991, abandoned.

[30] Foreign Application Priority Data

Sep. 6, 1990 [JP] Japan .................................. 2-238424

[51] Int. Cl.$^5$ ........................ B01D 61/14; B01D 61/22
[52] U.S. Cl. ..................................... 210/641; 210/645; 210/651; 210/652
[58] Field of Search .................... 424/423, 426; 514/2, 514/21; 530/350, 395, 840; 210/634, 644, 645, 649, 650-652, 641

[56] References Cited

U.S. PATENT DOCUMENTS

| | | | |
|---|---|---|---|
| 4,434,094 | 2/1984 | Seyedin et al. | 260/112 |
| 4,455,256 | 6/1984 | Urist | 260/112 |
| 4,743,259 | 5/1988 | Bolander et al. | 623/16 |
| 5,011,691 | 4/1991 | Oppermann et al. | 514/21 |

FOREIGN PATENT DOCUMENTS

| | | |
|---|---|---|
| 0182483 | 5/1986 | European Pat. Off. |
| 0366029A3 | 5/1990 | European Pat. Off. |

OTHER PUBLICATIONS

Journal of Biomedical Materials, 24:639 (1990).
M. Urist et al., Methods in Enzymology, 146:294 (1987).

Primary Examiner—Frank Sever
Attorney, Agent, or Firm—David G. Conlin; George W. Neuner; Peter F. Corless

[57] ABSTRACT

A process for preparing an osteogenesis promoting substance, which comprises extracting a demineralized bone powder with a solution of chaotorpic reagent, subjecting the extracted solution to ultrafiltration to collect a fraction containing substances ranging from 1,000 to 100,000 daltons as molecular weight, dialyzing the collected fraction and collecting the water-insoluble fraction from the dialyzing liquid. The osteogenesis promoting substance prepared by the present invention is useful as a bone repairing agent and a bone grafting agent.

8 Claims, No Drawings

PROCESS FOR PREPARING OSTEOGENESIS PROMOTING SUBSTANCE

This is a continuation of copending application Ser. No. 07/755,007, filed on Sep. 5, 1991, abandoned.

BACKGROUND OF THE INVENTION

1. Field of the Invention

The present invention relates to a process for preparing an osteogenesis promoting substance, which is useful as a bone repairing agent and a bone grafting agent in the field of surgery, orthopedic surgery and dentistry.

2. Description of the Prior Art

Conventionally, bone grafting in a living body is performed generally by autografting with a bone of the patient himself. However, the bone thus available for autografting is limited in quantity, while the patient must undergo surgery twice for the removal of the bone and the transplantation thereof and therefore suffers pain.

To overcome the drawback of autografting, it has been attempted to use a demineralized powder of organic matrix from the bone of a mammal (hereinafter referred to as "demineralized bone powder") to be implanted in the living body to cause the formation of an autogenous bone (Glowacki et al., Lancet, May 12, 1981). The demineralized bone powder contains several kinds of local osteogenesis promoting substances. When the powder is implanted in the living body, these osteogenesis promoting substances are systematically combined with one another at each step of ossification to for a new bone. First, granulations are formed around the particles of the demineralized bone powder through a vital reaction. Subsequently, mesenchymal cells in the living body are drawn to the surfaces of the particles of the powder by a chemotactic factor present in the bone powder and are differentiated into cartilage cells by a differentiation promoting factor present in the powder. When blood capillaries are formed in the granulation tissue, the cartilage cells die. The mesenchymal cells are differentiated into osteoblasts by a factor released from the cartilage cells and a factor released from the powder. The osteoblasts secrete collagen into the interstices between the particles of the bone powder, further calcifying the secreted collagen, with the result that a normal bone is formed in the interior of the granulation tissue. The bone thus formed undergoes a metabolic turnover as a normal bone.

However, the demineralized bone powder forms a new bone in the living body only in the case where the powder prepared from a bone from a species same as the recipient is implanted. A satisfactory bone will not always be formed owing to the inherent antigenicity in the case where the powder is prepared from a bone from a species different from the recipient. There is a limited availability of material when the powder is prepared from a bone from a homozoic species to produce a bone grafting agent, especially the species is human being. In view of the above problem, an attempt has been made to synthesize the osteogenesis promoting substances. The synthesis includes extracting and purifying the osteogenesis promoting substances, determining the amino acid sequence thereof, and synthesizing the substances by a gene recombination or the like [Wang, E.A. et al., Proc. Natl. Acad. Sci. USA, 87, 2220(1990); Bentz, H. et al., J. Biol. Chem., 264, 20805(1989); Luyten, F.P. et al., J. Biol. Chem., 264, 13377(1989); Sampath, T.K. et al., Calcif. Tissue Int., 46, Suppl. 2, A46(1990)].

An isolation method of an osteogenesis promoting substance is disclosed, for example, Methods in Enzymology, 146, 294-312 (1987) and in Journal of Biomedical Materials Research, 24, 639-654 (1990).

A normal ossification is conducted by the action of many osteogenesis promoting substances which are present in the bone matrix and systematically combined with one another, whereas a single osteogenesis promoting substance obtained as above affords remarkably weak or no osteogenic activity.

SUMMARY OF THE INVENTION

The present invention provides a process for preparing an osteogenesis promoting substance which is convenient and shows excellent yield, wherein a great number of osteogenesis promoting substances contained in a bone demineralized powder of an animal are extracted per se, and at the same time, ossification inhibiting substances special to the extracted substances are separated therefrom.

The present invention thus provides a process for preparing osteogenesis promoting substances, which comprises extracting a demineralized bone powder with a solution of chaotropic reagent, subjecting the extracted solution to ultrafiltration to collect a fraction containing substances ranging from 1,000 to 100,000 daltons as molecular weight, dialyzing the collected fraction and collecting the water-insoluble fraction from the dialyzing liquid.

PREFERRED EMBODIMENT OF THE INVENTION

A preferable bone serving as a material for preparing the demineralized bone powder is the one obtained from a species same as a host to which the bone is implanted. In the case where the host is human being, the shaft of the long bone of a mammal such as pig, sheep, horse, rabbit or bovine, especially neonatal calf, is desirable.

The demineralized bone powder can be prepared, for example, by the following method. The bone to be used as the material is cut and crushed, and the soft tissue is removed from the bone fragments. The resultant is washed with water, and then repeatedly with an organic solvent such as ethanol and ether to remove water and fat. The resulting bone fragments are pulverized to a suitable particle size. The particulate bone is then demineralized with hydrochloric acid, ethylenediaminetetraacetic acid or the like, washed with water, then repeatedly washed with an organic solvent and thereafter dried, giving the desired bone powder. The bone of a neonatal calf, when to be used, is collected immediately after the animal is killed, and is frozen for preservation. The bone shaft is cut off and roughly crushed. After removing the soft tissue from the bone fragments, the fragments are washed with water, then repeatedly washed with ethanol and ether to remove water and fat. With cooling, the resulting bone fragments are promptly pulverized to a suitable particle size. The particulate bone is then demineralized with hydrochloric acid, then washed with water, further washed repeatedly with ethanol and ether, and dried. The powder thus obtained is preferably about 75 to about 450 micrometers in particle size.

The obtained demineralized bone powder is extracted with a solution of chaotropic reagent which is a substance for weakening the bond between proteins. An example of the effective chaotropic reagent is a guanidine hydrochloride or urea. Guanidine hydrochloride is preferable. When the guanidine hydrochloride, for example, is used for extraction, an aqueous solution of 1 to 5M guanidine hydrochloride is added to the demineralized bone powder in an amount of 10 to 50 liters per 1 kg of the powder, which is then stirred for 1 to 3 days at 0° to 10° C. A protease inhibitor such as N-ethylmaleimide may be added during the extraction. After the extraction, the bone powder is removed by filtration.

The extracted solution thus obtained is purified with a 1,000 daltons cutoff ultrafilter followed by a 100,000 daltons cutoff ultrafilter. By the ultrafiltration of extract, a fraction molecular weight of less than 1,000 daltons and a fraction molecular weight of over 100,000 daltons are removed. Preferably, a hollow fibrous ultrafiltration membrane of polysulfone is employed for the 1,000 daltons cutoff ultrafilter. A 10,000 daltons cutoff ultrafilter can also be used, because most of the osteogenesis promoting substances are of 10,000 to 100,000 daltons, and a significant amount (approximately 30 to 40%) of substances (1,400 daltons) remains in a concentrated solution when the extracted solution is subjected to ultrafiltration with the 10,000 daltons cutoff ultrafilter, for example, P 10 hollow fibrous cartridge manufactured by Amicon, U.S.A. Ultrafiltration using the hollow fibrous ultrafiltration membrance of polysulfone is usually conducted under a pressure of 0.5 to 1.5 Kg/cm$^2$ for concentrating the extracted solution concentrated solution is then subjected to ultrafiltration using a 100,000 daltons cutoff ultrafilter. A 100,000 daltons cutoff ultrafiltration membrane of cellulose is preferably used for the 100,000 daltons cutoff ultrafilter. Ultrafiltration using the ultrafiltration membrane of cellulose is generally conducted under a pressure of 3.0 to 4.0 Kg/cm$^2$ for collecting the filtrate. The fraction containing the molecules of more than 100,000 include immunogen which inhibits ossification and ossification inhibiting substances, and hence will be gelled in a dialysis tube during dialysis.

The obtained filtrate (fraction containing substances ranging from 1,000 to 100,000 daltons as molecular weight) is poured into the dialysis tube to be dialyzed against water or a diluted buffer solution. A semipermeable membrane used for the dialysis tube preferably has a fraction molecular weight of about 1,000 to 8,000 daltons. An external solution for dialysis is preferably deionized water, but may be an aqueous ammonium bicarbonate solution having a low concentration (0 to 10 mM) and Tris buffer.

Subsequently, a water-insoluble fraction is collected, since a water-soluble fraction contains ossification inhibiting substances. The water-insoluble fraction, which is generally precipitated in the dialysis tube, can easily be taken out from the internal solution for dialysis by a known separating means such as centrifugation after dialysis.

The obtained water-insoluble fraction is lyophilized to give powders.

According to the process of the present invention, the procedure is convenient, and an osteogenesis promoting substance from a demineralized bone powder can be prepared in a short period of time and in a good yield.

The osteogenesis promoting substance obtained by the process of the present invention contains no ossification inhibiting substances to thereby effectively be used as a bone repairing agent and a bone grafting agent. For example, the osteogenesis promoting substance is applied to or incorporated into an artificial bone made of metal materials, ceramic materials or high polymer materials. The substance is thus applied or incorporated so that when the artificial bone is filled (implanted) in the contemplated bone deficient portion, the bone bonding regulating factors contained in the substance will be released in situ into the living tissue of the defective portion. For example, it is desired that the artificial bone has a surface property or surface structure suited to the application or incorporation of the substance. For example, the bone is made porous over the surface. Porous surfaces can be formed by a known method, for example, by bonding together granules of a particular material in the form of two layers with interstices provided between the granules, or by binding continuous metal fibers together in two layers as arranged randomly.

The osteogenesis promoting substance can be applied to or incorporated into such an artificial bone usually by dispersing the substance in a suitable dispersant, binder, diluent or the like (such as collagen, physiological saline, citric acid solution, acetic acid solution, hydroxyapatite, fibrin or a mixture thereof), coating or impregnating the bone with the dispersion, and drying the bone. The dispersion is prepared with a concentration sufficient to supply to the artificial bone an effective amount of the osteogenesis promoting substance serving as the active component.

It is desired that the substance be applied or incorporated into the artificial bone at the portion thereof to be firmly bonded to the living tissue of the bone deficient site. The example of the portion is the one which is in contact with the natural bone of the host when the artificial bone is implanted. Furthermore, the osteogenesis promoting substance is applied or incorporated into the artificial bone in an amount effective to fully firmly bond the artificial bone to the bone deficient portion of the host. The effective amount is, for example, about 0.1 to about 1.5 g/cm$^2$, preferably about 0.3 to about 0.5 g/cm$^2$, based on the area of the portion of the artificial bone to which the substance is to be applied or incorporated.

The osteogenesis promoting substance thus obtained can be used as an artificial bone fixing agent. The artificial bone fixing agent is prepared by incorporating the osteogenesis promoting substance as its active component into a dispersant, binder or diluent which is physiologically acceptable. The agent can be thus prepared by a known method. Other components (such as calcium) effective for osteogenesis may be added to the bone fixing agent. Instead of being applied or incorporated into artificial bones, the bone fixing agent of the invention can be used as filled in a clearance between the bone deficient portion of the host and the artificial bone implanted therein. In this case, the agent is used in such an effective amount as mentioned above.

EXAMPLES

The present invention will be described in greater detail with reference to the following examples, which nevertheless in no way limit the invention.

EXAMPLE 1

A demineralized bone powder was prepared by the method of Glowacki et al. (Glowacki, J. et al., Clinics in Plastic Surgery, 12, 233, 1985). Specifically stated, the shafts of the metacarpus and metatarsale of a bovine was cut off and roughly crushed, and the soft tissue and bone marrow were removed from the bone fragments, which were then repeatedly washed with cooled deionized water and further repeatedly washed with ethanol and diethyl ether. The bone fragments were then pulverized by an impact mill and thereafter screened to obtain a bone powder 75 to 450 micrometers in particle size. The bone powder was immersed in 0.5M hydrochloric acid for 3 hours for demineralization, then repeatedly washed with deionized water, ethanol and diethyl ether, and lyophilized to obtain demineralized bone powder. A new bone was not induced due to the rejection when the bovine demineralized bone powder was heterografted to a rat.

Described next is a preparation of a partially purified fraction of the osteogenesis promoting substance from the demineralized bone powder. The demineralized bone powder was stirred with a mixture of 4M guanidine hydrochloric acid (30 l per 1 kg), 10mM ethylenediamine tetraacetic acid (EDTA) and 10mM N-ethylmaleimide (NEM) (pH 6.8) for 48 hours at 4° C. for extraction. The extract was filtered through a filter paper, and thereafter, the filtrate was subjected to ultrafiltration using a 10,000 daltons cutoff hollow fiber cartridge (P10 hollow fiber cartridge manufactured by Amicon, U.S.A.) under pressure of 1.0 Kg/cm$^2$ for concentrating one-tenth of the original volume. The concentrated solution was subjected to ultrafiltration using a 100,000 daltons cutoff membrane filter (Diaflow membrane YM 100 manufactured by Amicon U.S.A.) under pressure of 3.8 Kg/cm$^2$ to give filtrate. The filtrate was poured into a dialysis tube (Spectrapor No. 3 manufactured by Spectrum Co., U.S.A., 3,500 daltons cut off) for dialyzing against cooled deionized water for 96 hours at 4° C., while exchanging the external solution for dialysis 9 to 10 times. The resulting solution was then centrifuged with high-speed cool centrifuger, 20PR-52D, RPR9-2 rotor (manufactured by Hitachi, JAPAN) for 10 minutes at 4,700×g to separate the water-insoluble fraction from the water-soluble fraction, each of which is then lyophilized to prepare powders.

REFERENCE EXAMPLE 1

In the preparation of Example 1, the internal solution for dialysis, containing both water-soluble and water-insoluble fractions, was lyophilized after dialysis to give powders.

REFERENCE EXAMPLE 2

In Example 1, the filtrate obtained after the extraction was subjected to ultrafiltration using 5,000 daltons cutoff membrane filter (Diaflow Membrane YM5 manufactured by Amicon, U.S.A.) under pressure of 3.8 Kg/cm$^2$. The concentrated solution thus obtained was dialyzed. The resulting solution, containing both water-soluble and water-insoluble fractions, was lyophilized after dialysis to give powders.

Experiment 1

The lyophilized substance prepared in Reference Examples 1 and 2 was dissolved in 0.1% (V/V) trifluoro acetic acid, to which liquid atherocollagen solution having low immunogenicity (e.g., Cellmatrix LA., Nitta Gelatin Co., Ltd.) was added as a carrier in a suitable amount and mixed at 4° C. for 1 to 2 hours. Thereafter, the resultant solution was neutralized with 0.1 N-NaOH, lyophilized and compressed for molding to form a suitable pellet-like shape. The pellets were implanted to the subcutaneous portion of the breast of 4-week old male rat.

The implant was removed 3 weeks after the implantation. The formation of the new bone was confirmed by the soft X rays photograph of the implant and the observation of the section of the tissue. Calcium content in the ashed implant was measured for evaluating the formation degree of the new bone. The result was shown in Table 1.

TABLE 1

| Implanted Protein Amount | Lyophilized Substance in Ref. Ex. 2 | | Lyophilized Substance in Ref. Ex. 1 | |
|---|---|---|---|---|
| | n | Ca Content in Implant | n | Ca Content in Implant |
| 1 mg | | | 3 | 0.10 ± 0.03 mg |
| 2 mg | 5 | 0.54 ± 0.16 mg | 3 | 0.56 ± 0.09 mg |
| 5 mg | 5 | 0.58 ± 0.19 mg | 6 | 3.13 ± 0.63 mg |
| 10 mg | | | 3 | 3.92 ± 1.30 mg |
| 20 mg | 5 | 1.71 ± 0.60 mg | 3 | 5.34 ± 2.08 mg | average value ± standard error
n: number of animals to be used

As shown in Table 1, the lyophilized substance prepared in Reference Example 1 causes increase in calcium content in the implant depending upon the protein amount to be implanted within the range of 1 mg to 20 mg. The calcium content clearly shows a relatively higher value when the protein amount to be implanted is more than 5 mg, compared to the lyophilized substance prepared in Reference Example 2 in which the proteins having molecular weight of more than 100,000 daltons were not cut off with the ultrafilter. The manifestation ratio of the new bone induction by the latter fractions was 47/64 when the protein amount to be implanted was more than 2 mg, while that by the former fractions was 48/48 when the protein amount was similarly more than 2 mg. Rejection phenomenon was not observed by a histlogical retrieval when the lyophilized substance prepared in Reference Example 2 was implanted. Further, normal bone tissue was observed comprising calcified bone including osteocytes as well as an osteoid tissue produced from an osteoblast and bone marrow, when the lyophilized substance prepared in Reference Example 2 was implanted.

There was no activity in the fraction which contains proteins cut off with ultrafiltration and having molecular weight of more than 100,000 daltons. The abovementioned fraction was added to the lyophilized substance prepared in Reference Example 1 to be similarly implanted, resulting in that the calcium content in the implant was inhibited from increasing depending upon the amount of the added fractions (Table 2).

TABLE 2

| Implanted Fractions | n | Calcium Content in the Implant |
|---|---|---|
| A: 5 mg | 5 | 2.60 ± 0.29 mg |
| A: 5 mg + B: 2.5 mg | 5 | 1.98 ± 0.21 mg |
| A: 5 mg + B: 5 mg | 5 | 1.00 ± 0.18 mg |
| A: 5 mg + B: 10 mg | 5 | 0.50 ± 0.14 mg |
| B: 5 mg | 5 | 0.01 ± 0.002 mg |

A: lyophilized substance prepared in Reference Example 1
B: fraction containing proteins having molecular weight more than 100,000 daltons which were cut off with ultrafiltration
n: number of animals to be used

Experiment 2

Evaluations were made by the same manner as in the Example 1 in the ability for inducing new bone of the lyophilized substance containing water-soluble fraction and that containing water-insoluble fraction prepared in Example 1. The result was shown in Table 3.

TABLE 3

| Implanted Fractions | n | Calcium Content in the Implant |
|---|---|---|
| A: 5 mg | 4 | 1.53 ± 0.62 mg |
| B: 5 mg | 4 | 5.02 ± 0.56 mg |
| B: 5 mg + C: 1 mg | 4 | 3.42 ± 0.53 mg |
| B: 5 mg + C: 5 mg | 4 | 1.62 ± 0.30 mg |
| C: 5 mg | 4 | 0.02 ± 0.003 mg |

A: lyophilized substance prepared in Reference Example 1
B: lyophilized substance containing water-insoluble fraction prepared in Example 1
C: lyophilized substance containing water-soluble fraction prepared in Example 1
n: number of animals to be used As shown in Table 3, the water-insoluble fraction prepared in Example 1 exhibited stronger activity compared to the mixture of water-insoluble and water-soluble fractions prepared in Reference Example 1, when the protein amount to be implanted was 5 mg. The water-soluble fraction possesses no activities, with the result that the addition of the water-soluble fraction (5 mg) to the water-insoluble fraction (5 mg) decreases the calcium content in the implant portion to the amount obtained when the lyophilized substance (5 mg) prepared in Reference Example 1 was implanted.

What is claimed is:

1. A process for preparing an osteogenesis promoting substance, by steps other than affinity chromatography, said steps comprising extracting a demineralized bone powder with a solution of chaotropic reagent, subjecting the extracted solution to ultrafiltration to collect a fraction containing substances ranging from 10,000 to 100,000 daltons as molecular weight, dialyzing the collected fraction and collecting the water-insoluble fraction from the dialyzing liquid.

2. A process as claimed in claim 1 wherein the demineralized bone powder is the one obtained from bovine or neonatal calf bone.

3. A process as claimed in claim 2 wherein an aqueous 1 to 5M guanidine hydrochloride solution is used for extraction in an amount of 10 to 50 liters per 1 Kg of the demineralized bone powder.

4. A process as claimed in claim 1 wherein the solution of chaotropic reagent is an aqueous guanidine hydrochloride solution.

5. A process as claimed in claim 1 wherein the extraction is conducted in the presence of a protease inhibitor.

6. A process as claimed in claim 1 wherein the ultrafiltration is conducted by use of a 10,000 daltons cutoff ultrafilter and a 100,000 daltons cutoff ultrafilter.

7. A process as claimed in claim 1 wherein the dialysis is conducted by use of a dialysis tube composed by a semipermeable membrane having a fraction molecular weight of about 1,000 to 8,000 daltons and an external solution of deionized water.

8. A process as claimed in claim 1 wherein the water-insoluble fraction is collected by centrifugation and further lyophilized to give powders.

* * * * *

UNITED STATES PATENT AND TRADEMARK OFFICE
CERTIFICATE OF CORRECTION

PATENT NO. : 5,244,577

DATED : September 14, 1993

INVENTOR(S) : Kohei Notoya, Keiji Yoshida, and Iwao Yamazaki

It is certified that error appears in the above-identified patent and that said Letters Patent is hereby corrected as shown below:

In column 3, line 25, please delete "subjectcd" and insert therefor --subjected--.

In column 6, line 41, please delete "histlogical" and insert therefor --histological--.

Signed and Sealed this

Twenty-fourth Day of May, 1994

Attest:

BRUCE LEHMAN

Attesting Officer

Commissioner of Patents and Trademarks